(12) United States Patent
Horst

(10) Patent No.: US 6,472,222 B2
(45) Date of Patent: Oct. 29, 2002

(54) METHOD OF ESTIMATING RATE OF NICOTINE METABOLISM IN INDIVIDUALS

(75) Inventor: W. Dale Horst, Newton, KS (US)

(73) Assignee: Via Christi Research, Inc., Wichita, KS (US)

( * ) Notice: Subject to any disclaimer, the term of this patent is extended or adjusted under 35 U.S.C. 154(b) by 0 days.

(21) Appl. No.: 09/250,676

(22) Filed: Feb. 16, 1999

(65) Prior Publication Data

US 2001/0039054 A1 Nov. 8, 2001

(51) Int. Cl.$^7$ .............................................. G01N 33/48
(52) U.S. Cl. ...................... 436/96; 436/106; 436/815; 436/804; 422/61; 422/89
(58) Field of Search ...................... 422/61, 89; 436/92, 436/106, 133, 804, 808, 96, 815

(56) References Cited

U.S. PATENT DOCUMENTS

| | | |
|---|---|---|
| 5,334,502 A | 8/1994 | Sangha |
| 5,380,492 A | 1/1995 | Seymour |
| 5,527,686 A | 6/1996 | Fitzpatrick et al. |
| 5,593,684 A | 1/1997 | Baker et al. |
| 5,707,872 A | 1/1998 | Eswara et al. |
| 5,780,051 A | 7/1998 | Eswara et al. |

OTHER PUBLICATIONS

John R. Hughes, M.D., et al., "Recent Advances in the Pharmacotherapy of Smoking" Journal of the American Medical Association, Jan. 6, 1999, vol. 281, No. 1.

Etter, Jean–Francois, et al., "Saliva Cotinine Levels in Smokers and Nonsmokers", American Journal of Epidemiology, vol. 151, No. 3, 2000.

Schneider, Sid J., et al., "Validating Reports of Nonsmoking with Breath and Saliva Samples: Your Checkup is in the Mail", Addictive Behaviors, vol. 8, pp. 187–191, 1983.

Etter, Jean–Francois, et al., "Collecting Saliva Samples by Mail", American Journal of Epidemiology, vol. 147, No. 2, 1998.

Foulds, Jonathan, et al., "The Stability of Cotinine in Unfrozen Saliva Mailed to the Laboratory", vol. 84, No. 7, Jul. 1994.

Greeley, Donald A., et al., "Stability of Salivary Cotinine sent through the U.S. Mail for Verification of Smoking Status", Addictive Behaviors, vol. 17, pp. 291–296, 1992.

Hall SM, Reus VI, Monoz RF, et al. "Nortriptyline and Cognitive–Behavioral Therapy in the Treatment of Cigarette Smoking" Arch Gen Psychiatry 1998; 55: 683–690.

Haxby DG: "Treatment of Nicotine Dependence" Am J Health–Syst Pharm. 1995; 52: 265–281.

Skaar K, Tsoh J, Cinciripini P, Wetter D, Prokhorov A, Gritz E: "Current Approaches in Smoking Cessation" Current Opinion in Oncology 1996; 8: 434–440.

Law M, Tang JL: "An Analysis of the Effectiveness of Interventions Intended to Help People Stop Smoking" Archives of Internal Medicine 1995; 155: 1933–1941.

Van Gilder TJ, Remington PL, Fiore MC: "The Direct Effects of Nicotine Use on Human Health" Wisconsin Medical Journal 1997; 96: 43–48.

Fiore MC, Smith SS, Jorenby DE, Baker TB: "The Effectiveness of the Nicotine Patch for Smoking Cessation" A meta–analysis. Journal of the American Medical Association 1994; 271: 1940–1947.

Miller GH, Golish JA, Cox CD: "A Physician's Guide to Smoking Cessation" Journal of Family Practice 1992; 34: 759–766.

Goldstein MG: "Bupropion Sustained Release and Smoking Cessation" J Clin Psychiatry 1998; 59: 66–72.

Orleans CT, Resch N, Noll E, et al: "Use of Transdermal Nicotine in a State–Level Prescription Plan for the Elderly" A first look at 'real world' patch users. Journal of the American Medical Association 1994; 271: 601–607.

Orleans CT, Schoenbach VJ, Wagner EH, et al: "Self–Help Quit Smoking Interventions: Effects of Self–Help Materials, Social Support Instructions, and Telephone Counseling" J. Consult Clin. Pyschol. 1991; 39: 439–448.

Fagerstrom KO: "Measuring Degree of Physical Dependence to Tobacco Smoking With Reference to Individualization of Treatment" Addict. Behav. 1978; 3: 235–41.

Benowitz NL, Zevin S, Jacob P, III: "Sources of Variability in Nicotine and Cotinine Levels with use of Nicotine Nasal Spray, Transdermal Nicotine, and Cigarette Smoking" Br J Clin. Pharmacol 1997; 43: 259–267.

Paoletti P, Fornai E, Maggiorelli F, et al: "Importance of Baseline Cotinine Plasma Values in Smoking Cessation: Results from a Double–Blind Study with Nicotine Patch" Eur Respir. J 1996; 9: 643–651.

Sachs DP: "Effectiveness of the 4–mg Dose of Nicotine Polacrilex for the Initial Treatment of High–Dependent Smokers" Archives of Internal Medicine 1995; 155: 1973–1980.

Nakajima M, Yamamoto T, Nunoya K–I, et al: "rose of Human Cytochrome P4502A6 in c–oxidation of Nicotine" Drug Metab. Dispos. 1996; 24: 1212–1217.

(List continued on next page.)

Primary Examiner—Lyle A. Alexander
(74) Attorney, Agent, or Firm—Shook Hardy & Bacon

(57) ABSTRACT

A simple screening method is provided for determining biological variations among individuals in a smoking cessation program so that a therapy regimen can be adjusted appropriately for each individual. The method includes the steps of having an individual intake a predetermined dose of nicotine, taking a saliva sample at a predetermined time subsequent to intake of the dose of nicotine, and measuring the nicotine and cotinine levels in the sample. Thereafter, a ratio is calculated which includes both the nicotine and cotinine levels as an indicator of the rate of nicotine metabolism of the individual being screened.

6 Claims, 1 Drawing Sheet

OTHER PUBLICATIONS

Berkman CE, Park SB, Wrighton SA, Cashman JR: "In Vitro–In Vivo Correlations of Human (s)–nicotine Metabolism" Biochem Pharmacol 1995; 50: 565–570.

Messina ES, Tyndale RF, Seller EM: "A Major Role of CYP2A6 in Nicotine c–oxidation by Human Liver Microsomes" J Pharmacol. Exp. Ther. 1997; 282: 1608–1614.

Benowitz N, Porchet H, Jacob P, III: "Pharmacokinetics, Metabolism, and Pharmacodynamics of Nicotine" In: Nicotine Psychopharmacology. Wonnacott S, Russell MAH, Stoleman IP, eds. Oxford: oxford University Press, 1990; 112–157.

Benowitz NL and Jacob P, III: "Individual Differences in Nicotine Kinetics and Metabolism in Humans" Rapaka RS, Chiang N, and Martin BR. NIDA Research Monograph 173, 48–64. 1997. Rockville, MD, U.S. Dept. of Health and Human Services, National Institutes of Health. Pharmacokinetics, Metabolism and Pharmaceutics of Drugs of Abuse. (GENERIC) Ref. Type: Serial (Book, Monograph).

Pianezza ML, Seller EM, Tyndale RF: "Genetically Variable CYP2A6 Influences Smoking Behavior" Clin. Pharmacol. Ther. 1998; 63: 171–171.

Russell MAH: "Nicotine Intake and its Regulation by Smokers" In: Tobacco Smoking and Nicotine; a neurobiological approach. Martin WR, et al, eds. New York: Plenum Press, 1987; 25–50.

Benowitz NL, Jacob P, III: "Nicotine Renal Excretion Rate Influences Nicotine Intake During Cigarette Smoking" J Pharmacol. Exp. Ther. 1985; 234: 153–155.

McMorrow MJ, Foxx RM: "Nicotine's Role in Smoking: An Analysis of Nicotine Regulation" Psychologica Bulletin 1983; 93: 302–327.

Greenland S, Satterfield MH, Lanes SF: "A Meta–Analysis to Assess the Incidence of Adverse Effects Associated with the Transdermal Nicotine Patch" Drug Safety 1998; 18: 297–308.

Zeidenberg P, Jaffe JH, Kanzler M, Levitt MD, Langone JJ, Van Vunakis H: "Nicotine: Cotinine Levels in Blood During Cessation of Smoking" Comprehensive Psychiatry 1977; 18: 93–101.

Feyerabend C, Ings RM, Russell MAH: "Nicotine Pharmacokinetics and its Application to Intake from Smoking" Br. J. Clin. Pharmacol. 1985; 19: 239–247.

Haley NJ, Axelrad CM, Tilton KA: "Validation of Self–Reported Smoking Behavior: Biochemical Analyses of Cotinine and Thiocyanate" American Journal of Public Health 1983; 73: 1204–1207.

Langone JJ, Gjika HB, Van Vunakis H: "Nicotine and its Metabolites" Radioimmunoassays for Nicotine and Cotinine. Biochemistry 1973; 12: 5025–5030.

Benowitz NL, Jacob PI, Denaro C, Jenkins R: "Stable Isotope Studies of Nicotine Kinetics and Bioavailability" Clin. Pharmacol. Ther. 1991; 49: 270–277.

Feyerabend C, Russell MAH: "A Rapid Gas–Liquid Chromatographic Method for the Determination of Cotinine and Nicotine in Biological Fluids" J. Pharm. Pharmacol. 1990; 42: 450–452.

Rose JE, Levin ED, Benowitz N: "Saliva Nicotine as an Index of Plasma Levels in Nicotine Skin Patch Users" Therapeutic Drug Monitoring 1993; 15: 431–435.

METHOD OF ESTIMATING RATE OF NICOTINE METABOLISM IN INDIVIDUALS

CROSS-REFERENCE TO RELATED APPLICATIONS

"Not Applicable".

STATEMENT REGARDING FEDERALLY SPONSORED RESEARCH OR DEVELOPMENT

"Not Applicable".

BACKGROUND OF THE INVENTION

The present invention relates generally to smoking cessation methods and, more particularly, to a method for determining biological variations among individuals in a smoking cessation program so that a therapy regimen can be adjusted appropriately for each individual.

In the decades since the Surgeon General's report associating smoking with serious diseases and increased death rates, a variety of smoking cessation programs have been employed to help smokers stop smoking. Initially, such programs consisted primarily of behavior modification strategies. Subsequently, nicotine replacement therapy (NRT) was developed in the form of nicotine-containing gum and transdermal patches for use as aids during smoking cessation. Later still, the antidepressant, bupropion was approved for smoking cessation therapy, and was marketed under the trademark ZYBAN®. Over the past decade several programs have been offered which combine behavioral and pharmacological therapies.

Smoking a cigarette causes a rapid but short-lived rise in plasma nicotine. Presumably, the trigger to smoke again occurs as one's nicotine level falls sufficiently to produce a "craving" sensation. Thus, the height and duration of the nicotine "spike" has a major impact on smoking frequency, as well as other behaviors such as puff depth and duration, and nicotine content of the preferred brand of cigarette.

Several lines of evidence suggest that smoking behavior by individual smokers is adapted to produce a pharmacologically relevant concentration of nicotine in the brain and that this level is fairly uniform across individuals, regardless of whether they metabolize nicotine quickly or slowly. Thus smokers with a rapid rate of nicotine metabolism are likely to increase their nicotine intake by smoking frequently, smoking brands high in nicotine, and taking deeper, longer inhalations. Conversely, slow nicotine metabolizers would be expected to exhibit smoking behavior that limits nicotine intake. This has been demonstrated in a recent study where smokers genetically deficient in cytochrome 2A6 were found to smoke less than individuals with normal levels of enzyme activity. See, Pianezza M. L. et al., *Genetically Variable CYP2A6 Influences Smoking Behavior*, in American Society for Clinical Pharmacology and Therapeutics 63, 171 (1998).

A technical problem of known smoking cessation programs is that they are designed to be "one size fits all". Conventional programs do not provide for individual preferences or biological variations, although the need for individualization of treatment as been realized for some time and has been shown to enhance treatment efficacy. Recent studies have more precisely identified the biological differences among individual smokers suggesting the means for developing and designing improved therapies for treating nicotine addiction.

The individual variation in nicotine metabolism and intake by smokers has important implications in applying smoking cessation strategies. For example, NRT is often used at a single standard dose, which for some individuals may be inappropriate and lead to treatment failure. In the case of slow nicotine metabolizers, a standard dose may be too high, leading to undesirable side effects and to therapeutic failure by maintaining a plasma nicotine level above that which was present during smoking. In contrast, rapid nicotine metabolizers may fail on standard NRT doses because plasma nicotine levels are too low to control cravings.

Although bupropion, as an alternative to NRT, is not metabolized by the same route as nicotine, and thus could serve as an alternative to NRT, bupropion does have contraindications that may preclude its use in all individuals attempting to quit smoking. Thus, a simple inexpensive means of estimating individual rates of nicotine metabolism and intake would be of invaluable assistance to the therapist in assigning a pharmacological intervention with the greatest probability of success.

Cotinine is the metabolic product formed by the action of cytochrome 2A6 on nicotine. Unlike nicotine, which exhibits a biphasic elimination with relatively short half-lives of approximately 10 minutes and 2 hours, cotinine has a long half-life of approximately 19 hours. Thus, cotinine plasma levels are relatively stable and reflect the extent of nicotine conversion by 2A6. Because of its pharmacokinetic properties, cotinine has been widely used to determine the presence of nicotine intake. In pharmacokinetic studies, plasma levels of cotinine in smokers have been shown to be strongly correlated with nicotine dose. Because of cotinine's relatively long half-life, the timing of the cotinine sampling with respect to smoking activity is not critical.

BRIEF SUMMARY OF THE INVENTION

It is an object of the present invention to solve the technical problem left unaddressed by the prior art, and to provide a method for determining biological variations among individuals in a smoking cessation program so that a therapy regimen can be adjusted appropriately for each individual.

In accordance with this and other objects evident from the following description of a preferred embodiment of the invention, a method of estimating the rate of nicotine metabolism in an individual includes the steps of having the individual intake a predetermined dose of nicotine, taking a saliva sample from the individual at a predetermined time subsequent to intake of the nicotine, and measuring both the nicotine and cotinine levels in the sample. Thereafter, a ratio including the nicotine and cotinine levels is calculated as an indicator of the rate of nicotine metabolism of the individual, and can be used to make adjustments to the individual's smoking cessation therapy regimen.

By providing a construction in accordance with the present invention, numerous advantages are realized. For example, although evidence exists that plasma cotinine levels reflect nicotine intake, the ratio of plasma nicotine to plasma cotinine concentrations provides a more sensitive measure of estimating nicotine intake or smoking behavior. The reason for this is that plasma nicotine and cotinine concentrations move in opposing directions depending on individual rates of nicotine metabolism. An individual with a rapid rate of nicotine metabolism will smoke more to maintain a pharmacologically active level of nicotine such that their steady state levels of cotinine will be high. After smoking, their levels of nicotine will be lower than normal. Conversely, a slow nicotine metabolizer screened shortly after smoking would present low levels of cotinine and relatively high levels of nicotine compared to the individual who is a rapid nicotine metabolizer.

Thus, a ratio of plasma cotinine/nicotine concentrations obtained soon after smoking provides an estimate of an individual's metabolic rate for nicotine with an accuracy sufficient to assign an appropriate pharmacological intervention to assist in smoking cessation.

BRIEF DESCRIPTION OF THE SEVERAL VIEWS OF THE DRAWING

The preferred embodiment of the present invention is described in detail below with reference to the attached drawing, wherein.

DETAILED DESCRIPTION OF THE INVENTION

A preferred method of estimating the rate of nicotine metabolism in an individual broadly includes the steps of having the individual intake a predetermined dose of nicotine, taking a saliva sample from the individual at a predetermined time subsequent to intake of the dose of nicotine, measuring the nicotine and cotinine levels in the sample, and calculating a ratio including both the nicotine and cotinine levels as an indicator of the rate of nicotine metabolism of the individual.

The inventive method is preferably carried out during screening of the individual for participation in a smoking cessation treatment program having a regimen incorporating both behavior modification and drug treatment strategies. As such, information in addition to that required for practicing the present invention is gathered during the screening process in order to enable the practitioner administering the program to best tailor treatment to the individual being considered.

Figure 1:
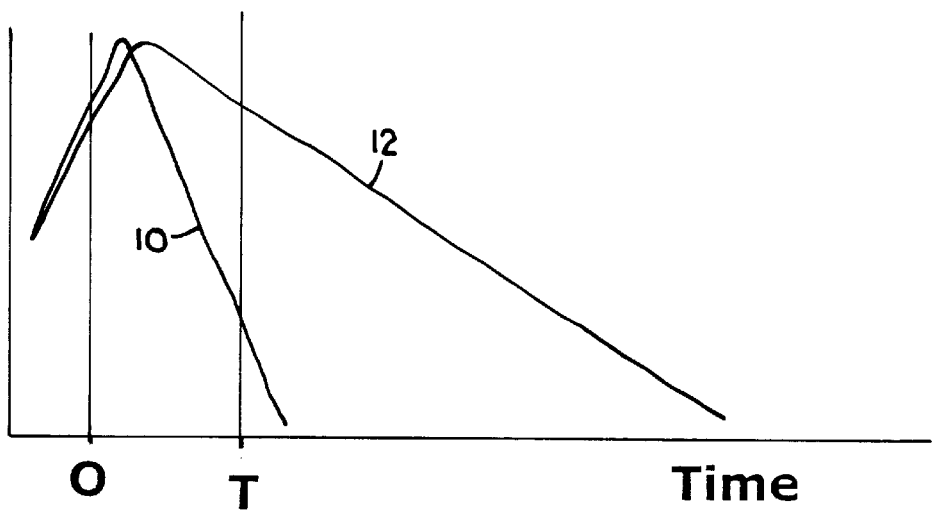
FIG. 1 is a graph illustrating nicotine levels over time in two different types of individuals.
Figure 2:
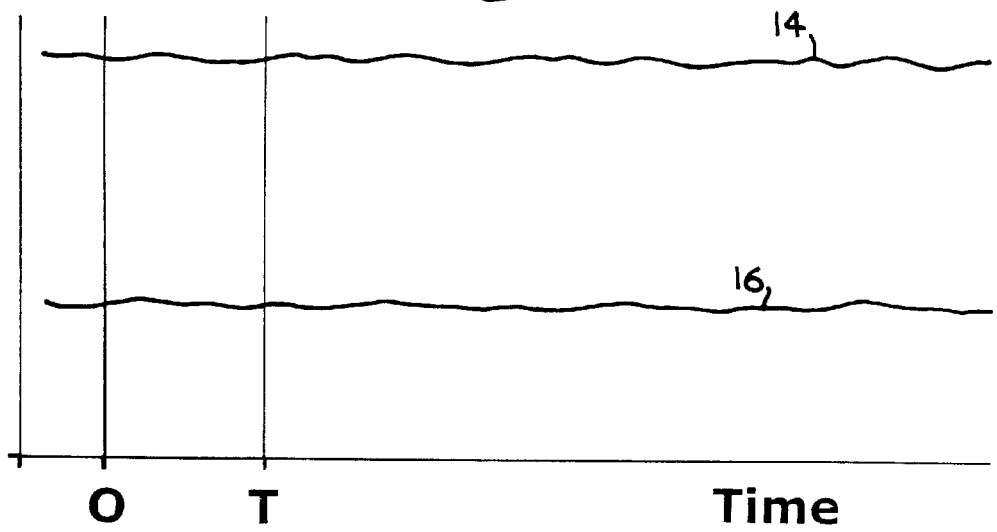
FIG. 2 is a graph illustrating cotinine levels over time in two different types of individuals.

Initially, the individual is asked to remove lipstick and other substances from their lips, and to smoke a single cigarette. Alternately, any other mechanism such as a patch or the like may be employed to administer a predetermined dose of nicotine to the individual during the screening process. Regardless of the manner of administration of the dose of nicotine, the individual is carefully monitored during dosing so that the time from the final puff of cigarette or final administration of nicotine can be measured. As shown in FIGS. 1 and 2, the time at which this final puff is taken is denoted "O." After a delay of predetermined duration, which can range from less than one minute to as many as thirty minutes from the final puff of cigarette or final administration of nicotine, and which preferably ranges between two and ten minutes from the final puff of cigarette or final administration of nicotine, and most preferably of five minutes therefrom, the individual dispenses saliva through a drinking straw into a suitable vial or tube.

If the saliva sample is taken too soon after the final puff of cigarette or final administration of nicotine, the difference in nicotine levels of fast and slow nicotine metabolizers is too slight to be distinguishing. If the delay is too long after the final puff of cigarette or final administration of nicotine, there will be no nicotine left in the sample, regardless of whether the individual is a rapid or slow nicotine metabolizer. Thus, it is important for the delay to be within the noted ranges in order to provide results that permit rapid and slow nicotine metabolizers to be distinguished from one another.

The precision of the sample collection with respect to the timing of the smoking or nicotine dosing is extremely important in this procedure since nicotine levels change rapidly during this time. It is not so important what the delay is, but rather that the delay be consistent from individual to individual so that the information gathered for all individuals will be consistent. As such, regardless of the length of delay chosen, it must be repeated accurately and consistently in all screening carried out under the method in order to provide a useful indication of the relative rates of nicotine metabolism in the individuals screened.

The sample obtained from the individual is labeled and analyzed in order to determine the nicotine and cotinine levels in the sample. Preferably, radioimmunoassay or gas chromatography processes are used to make these determinations. However, any other known method of determining the nicotine and cotinine levels in the saliva sample may be used without departing from the scope of the present invention. For example, it is also possible to use isotopic derivatives of nicotine to determine the nicotine and cotinine levels in the sample, if desired. Gas chromatography offers the particular advantages of providing a rapid, sensitive, and economical method for making these determinations, and is adaptable to large volumes of assays.

Although it would be possible to collect plasma samples from the individual being screened, and to determine the nicotine and cotinine levels from the plasma samples directly, several advantages are realized from using a saliva sample, as provided for herein. For example, the collection of saliva samples is non-invasive and does not require a medical procedure. Thus, it can be accomplished by the individual himself during screening, and is more user friendly for this reason. In addition, the taking of a saliva sample does not require any particular skills such as phlebotomy, and may provide data more representative of arterial concentrations than other types of samples. Because the levels of nicotine and cotinine in saliva and plasma are highly correlated, saliva samples are preferred for estimating plasma cotinine/nicotine levels in individual subjects.

Once the nicotine and cotinine levels in the saliva sample of the individual are determined, a ratio of the cotinine to nicotine is calculated, and this ratio is used as a part of the screening process, along with other information such as the individual's smoking pattern and medical history, with an emphasis on the presence of cardiovascular disease, diabetes, pregnancy, and concomitant medication use. Preferably, the ratio represents the cotinine level in the sample to the nicotine level such that a high ratio represents a rapid nicotine metabolizer, and a low ratio represents a slow nicotine metabolizer. However, the ratio could also be represented by the nicotine level in the sample to the cotinine level, rendering the ratio inversely related to the rate of nicotine metabolism of the individual, i.e. a high ratio would be indicative of a slow nicotine metabolizer and a low ratio would represent a rapid metabolizer.

As shown in FIG. 1, the nicotine level in the sample taken from the individual will be dependent on whether the individual metabolizes nicotine rapidly, as represented by the line 10, or slowly, as represented by the line 12. As such, the level of nicotine detected in the individual at the predetermined time after dosing provides an accurate indication as to the rate at which the individual metabolizes nicotine relative to others who are screened in the same manner.

Because cotinine exhibits a relatively long half-life of approximately 19 hours, cotinine plasma levels are relatively stable and reflect the extent of nicotine conversion by 2A6. With reference to FIG. 2, the cotinine level in the sample taken from the individual will be correlated to whether the individual is a heavy smoker, as represented by the line 14, or a light smoker, as represented by the line 16.

If a rapid metabolizer, represented by line 10 in FIG. 1, who is also a heavy smoker as represented by line 14 in FIG. 2, is screened, the resulting cotinine/nicotine ratio is high relative to an individual who has relatively low nicotine and cotinine levels, as represented by lines 12, 16 in FIGS. 1 and 2, respectively. However, so long as the cotinine/nicotine ratio is calculated and applied consistently from individual to individual, it is unimportant whether the ratio is cotinine/nicotine or nicotine/cotinine.

Regardless of which ratio is used in the method, a qualified health care provider uses the ratio along with all of the other information gathered during the screening process to choose the most appropriate pharmacological agent for the individual. The prescreening information may also suggest that some individuals receive no pharmacological intervention. The cotinine/nicotine ratio will provide the major evidence concerning the individual's rate of nicotine metabolism, and the individual's smoking behavior will provide confirmatory information. An individual with a high cotinine/nicotine ratio is a rapid metabolizer, and will likely be a heavy smoker who uses brands of cigarettes which deliver high doses of nicotine, and who inhales deeply. The opposite would be true of an individual with a low ratio since such a ratio is representative of a slow metabolizer who likely is a light smoker who uses brands of cigarettes which deliver low doses of nicotine and who inhales less deeply.

Although the invention has been described with reference to the preferred embodiment illustrated in the attached drawing figures, it is noted that substitutions may be made and equivalents employed herein without departing from the scope of the invention as recited in the claims.

What is claimed is:

1. A method of estimating the rate of nicotine metabolism in an individual, the method comprising the steps of:
    having the individual intake a predetermined dose of nicotine;
    having the individual provide a saliva sample at a predetermined time subsequent to intake of the dose of nicotine;
    measuring the nicotine and cotinine levels in the sample;
    calculating a ratio of nicotine to cotinine levels wherein said ratio is calculated by dividing said nicotine level by said cotinine level; and
    using one of the ratio and the inverse of the ratio as an indicator of the rate of nicotine metabolism of the individual.

2. The method as recited in claim 1, wherein the step of having the individual intake a predetermined dose of nicotine includes having the individual smoke a cigarette.

3. The method as recited in claim 2, wherein the step of having the individual provide a saliva sample is performed at a predetermined time subsequent to conclusion of the smoking step.

4. The method as recited in claim 1, wherein the step of measuring the nicotine and cotinine levels in the sample is performed using isotopic derivatives of nicotine.

5. The method as recited in claim 1, wherein the step of measuring the nicotine and cotinine levels in the sample is performed using a radioimmunoassay.

6. The method as recited in claim 1, wherein the step of measuring the nicotine and cotinine levels in the sample is performed using gas chromatography.

* * * * *